US006861083B2

(12) United States Patent
Martel et al.

(10) Patent No.: US 6,861,083 B2
(45) Date of Patent: Mar. 1, 2005

(54) PROCESS AND APPARATUS FOR THE INTEGRAL UTILIZATION OF OIL-PRODUCING DRUPES, PARTICULARLY OLIVES, AND SPECIFIC PRODUCTS OBTAINED

(76) Inventors: Jean-Pierre Martel, 247 Allée Traversière, 06250 Mougins (FR); Olivier Farcot, Le Coulet, 04110 Reillamme (FR)

( * ) Notice: Subject to any disclaimer, the term of this patent is extended or adjusted under 35 U.S.C. 154(b) by 279 days.

(21) Appl. No.: 09/998,710

(22) Filed: Nov. 30, 2001

(65) Prior Publication Data

US 2002/0106431 A1 Aug. 8, 2002

(30) Foreign Application Priority Data

Dec. 1, 2000 (FR) .............................................. 00 15558

(51) Int. Cl.⁷ ............................. A23N 4/00; A23P 1/00
(52) U.S. Cl. ........................ 426/481; 99/483; 99/538; 99/547; 426/482; 426/485; 426/520
(58) Field of Search ................................ 426/241, 481, 426/482, 485, 486, 520, 615; 99/451, 483, 538, 547, 565

(56) References Cited

U.S. PATENT DOCUMENTS

| 4,485,732 A | * 12/1984 | Goudard ...................... 99/549 |
| 4,732,771 A | * 3/1988 | Bushman .................... 426/482 |
| 4,925,691 A | * 5/1990 | Cimperman ................ 426/485 |

FOREIGN PATENT DOCUMENTS

| DE | 803609 | 4/1951 |
| EP | 421956 | 4/1991 |
| FR | 569578 | 4/1924 |
| FR | 2422713 | 11/1979 |
| GB | 367751 | 2/1932 |
| GB | 1209675 | 10/1970 |
| WO | 94 00541 | 1/1994 |
| WO | 99 16322 | 4/1999 |
| WO | 00 23545 | 4/2000 |

OTHER PUBLICATIONS

R.S. Farag et al.: "Stabilization of Olive Oil by Microwave Heating" *International Journal of Food Sciences and Nutrition*. vol. 48, No. 6, 1997, pp. 365–371.

* cited by examiner

*Primary Examiner*—George C. Yeung
(74) *Attorney, Agent, or Firm*—Muserlian, Lucas and Mercanti

(57) ABSTRACT

A process and an apparatus for the processing of oil-producing drupes, notably olives, is described comprising at least one device (20, 24) for the processing of whole drupes which effects a physical destructuring with incipient detachment of the drupe pulp from the skins and stones, under conditions which substantially avoid the oxidation mainly of the pulp's natural antioxidants; at least one device (42, 52; 110; 120, 124, 130, 134, 160, 170) for the physical separation and recovery (at 100) of the pulp essentially devoid of stones and advantageously skins, and (at 92, 96, 110) of the stones essentially devoid of pulp, advantageously with the skins, ly under conditions which substantially avoid oxidation; and at least one device (160, 170, 172, 174) for the separation and recovery of the pulp oil essentially devoid of stone oil and containing the pulp's natural antioxidants, thereby improving the purity and oxidation resistance of the pulp oil.

31 Claims, 3 Drawing Sheets

FIG.1 Process/product diagram

PROCESS AND APPARATUS FOR THE INTEGRAL UTILIZATION OF OIL-PRODUCING DRUPES, PARTICULARLY OLIVES, AND SPECIFIC PRODUCTS OBTAINED

The invention relates essentially to a process and an apparatus for the processing of whole fruits of the type comprising oil-producing drupes, to the products derived therefrom, especially a pure pulp oil, a whole or partially de-oiled pulp and volatile flavors specific to the fruit, and to a utilization of the co-products (woody shells, skins and kernels) made possible by the invention.

Drupes are understood according to the invention, from a botanical point of view, as stone fruits, i.e. fruits which comprise, from outside to inside, an epicarp, commonly called skin, a fleshy mesocarp, often commonly called pulp or flesh, and an endocarp, commonly called stone, which is formed of a woody shell and protects the seed, normally called kernel, contained inside the shell.

The invention applies especially to oil-producing drupes (containing oil in both the mesocarp and the kernel of the endocarp) such as the olive tree (Olea Europa), the oil palm (Elacis Guineesensis) and the avocado (Persea Americana), without excluding other oil-producing drupes.

In general terms the invention relates to all fruits of the type comprising oil-producing drupes for which the separation and preparation of the mesocarp apart from the other constituents of the fruit (epicarp and endocarp) constitute an improvement:

1) either for the purpose of extracting specific products contained in the mesocarp, such as the oily products, and utilizing both the resulting products (oil and partially de-oiled pulp) after separation;
2) or for using the mesocarp or pulp whole;
3) or, preferably, for rationally utilizing all the products derived from the whole fruit, from the epicarp to the endocarp, including the woody shells and kernels.

Within the framework of the invention, a further object is to effect the separation and differentiation of the different parts of the whole fruit while at the same time preserving their integrity for the purpose of utilizing their constituents and exploiting their inherent properties in uses of the type comprising power generation, industry, foodstuffs, cosmetics or pharmaceutics. The invention makes it possible to avoid the situation whereby the mixing of the prior art before the oil extraction and the non-differentiation of the different parts of the fruit create polluting effluents which have to be subjected to a specific treatment, detracting from the economics of the enterprise.

DESCRIPTION OF THE PRIOR ART

Since ancient times, olives have been ground whole and mixed in the air for a long time before being pressed to extract their oil.

The use of centrifugal separators is currently known for separating the solid, liquid and aqueous phases. The latest developments comprise, upstream, metal grinders with added disintegrators and mixers operating in the air for periods in the order of 30 to 40 minutes and in semicylindrical troughs provided with a double wall having a heating device to bring the ground whole olive paste to temperatures of between 25 and 30° C.

The disadvantages of the conventional manufacturing methods are listed below:

During grinding, whether in traditional grinding wheels or modern rotary grinders, the presence of air oxidizes the oil released from the cells, this oxidation being exacerbated in the first case by the duration of the operation or in the second case by the air stream induced by rapid rotation. Oxidation is responsible for degrading the quality of the oil throughout its shelf life.

As far as the mixers and triturators are concerned, their prolonged action produces oxidation phenomena inside the paste itself.

The grinding and mixing of the whole fruit over a long period in the presence of air and at a temperature of between 28 and 30° causes hydrolysis due to the high water content of the mesocarp, enzymatic lipolysis, and microbial lipolysis associated with the presence of a microflora on the epicarp. In fact, the time which elapses between the grinding of the olives and the moment of separation of the oil with water is not short enough to avoid these phenomena which degrade the oil.

Furthermore, this long period of time (30 to 40 minutes) at relatively high temperatures causes the fruit to lose the most volatile flavors which form part of the organoleptic architecture peculiar to each variety of olive.

Moreover, prior mixing of all the components of the fruit by grinding has several drawbacks:

The pulp oil is in contact, or mixed, with the fats contained in the epicarp, the shell oil and the kernel oil, all of which are more acidic and more prone to turning rancid. Although the first two can contribute to a deterioration of the flavors and tastes peculiar to the pulp oil, the oil contained in the kernel has applications in pharmacy and cosmetics for greater value than the pulp oil.

Apart from the loss of utilization of the components of the epicarp and the endocarp in each of their domains, the mixture called olive marc becomes a solid effluent which, even after a possible solvent extraction of the residual oil, currently represents a problem in terms of its own recycling. Likewise, the washes with water not only are responsible for the loss of hydrophilic principles, such as certain polyphenols, necessary for good preservation of the oil, but also generate effluents, called 'margines' (a mixture of vegetation water and fruit debris), which exacerbate the pollution problem already created by the vegetation water.

Different processes have been proposed for prior mechanical and hydraulic separation of the stones, but they are very long and favor oxidation. In addition, they have the disadvantages of the trituration and the mixing of the paste which follows it, even though they apply only to the pulp, and of the increase in the liquid effluent discharges.

Finally, it should be pointed out that the seasonal nature of the olive oil industry, the great variability of production and the limited hourly capacity of modern conventional equipment do not allow the installation of mills capable of coping with all the daily deliveries. It is therefore obligatory to store the fresh olives whole without spontaneous hydrolyses and enzymatic lipolysis mechanisms, such as described above during the processing, taking place in the fruit itself. Now, in practice, at peak harvest, the olives are not processed until several days after harvesting and are stored under conditions that initiate the degradation mechanisms described above, which are acknowledged to be largely responsible for tainting the oil (acidifying it and turning it rancid) and lowering the oil yields.

Objects of the Invention in its General Application to Oil-producing Drupes, Particularly Olives One main object of the invention is to tackle all the problems presented by the prior art, as described above.

Another main object of the invention is to propose a novel industrial concept for the processing of whole oil-producing drupes, particularly olives, which consists in changing from an industry centered only on extraction of the oil from the fruit to an industry for the overall processing of the whole fruit with a view to an integral utilization of the components of the fruit, without being entirely dependent on the seasonal nature of the whole fruit and on processing it fresh as soon as possible after harvesting.

Another main object of the invention is to solve the new technical problem which consists in the provision of a solution for improving the organoleptic properties of the oils from oil-producing drupes, particularly olives, their keeping time, their processing versatility and, in general terms, the utilization of the different parts of oil-producing drupes, particularly olives, oil-palm drupes and avocado drupes, naturally without excluding other oil-producing drupes.

Another main object of the present invention is to solve the new technical problem which consists in the provision of a solution for the processing of whole oil-producing drupes, particularly olives, in order to extract especially their oils, by a method of production which results in reducing or suppressing the effluents, utilizing the by-products and, preferably, favoring the self-sufficiency of the production unit in terms of the heat requirement.

All these objects are achieved for the first time within the framework of the present invention in a simple, safe and reliable manner which can be used on the industrial scale.

The invention also makes it possible to obtain by-products which can be used either as ingredients for foodstuffs for human or animal nutrition, particularly cattle feed, or for the manufacture of cosmetic or pharmaceutical products, or else as combustion materials from the fibers or woody shells of the stones.

Thus, according to a first feature, the present invention provides a process for the processing of oil-producing drupes as defined in claim 1.

Advantageous characteristics of this processing operation are also defined in the process subclaims, all these claims being incorporated as a whole in the description by way of reference.

In general terms, the invention relates to a process for obtaining such products which consists, after washing of the whole oil-producing drupes, in a preheating operation advantageously by means of microwaves, without excluding other methods of heating (conduction by means of heat-transfer fluid, electrical heating elements or direct low-pressure steam), in order to effect a rapid heating limited to the pulp (mesocarp), avoiding any cooking phenomena (time/temperature integration) and allowing at one and the same time a substantially complete destruction of the microbial flora contained on the epicarp or skin of the fruit and the deactivation of the enzymatic phenomena (hydrolysis and lipolysis). As regards microwaves, which act only on the water, the action on the peripheral flora is favored by the residual film of washing water.

The fruits are preferably preheated in a preheating enclosure comprising a microwave tunnel, rather than by the other heating methods, the reason being that, on a fresh fruit with a moisture content of 50% or more, microwaves cause the desired heating much more rapidly. Control of the heat front in the mesocarp or pulp and of the cooking phenomena is more precise and also, importantly for this type of product, the heating is applied preferentially to the water molecules, thereby preserving the other constituents of the pulp, especially the oil. However, for reasons of economics and electrical power installation, direct heating by means of expanded steam or indirect heating by means of heat-transfer fluid or an electrical heating element may be preferable for high hourly throughputs (in excess of 1 T/h). Furthermore, in this case, the recovery of the woody shells of the stones allows self-sufficiency in terms of heat on the production site. However, they can equally well be used as a fuel for driving an electric generator.

On leaving the continuous preheating tunnel, the drupes are introduced into a reduced-pressure enclosure for the purpose of causing the cellular tissues of the drupe pulp to burst. In this reduced-pressure enclosure, a mechanical separation is preferably carried out according to the invention, advantageously in its bottom part, said separation being effected by a mechanical separating device which completes the destructuring of the drupes by completing the detachment of the different components of the fruit (skin, pulp and stone) and a fine separation thereof, with the skins and stones remaining whole, by means of a mechanical effect, and the mechanical separation is carried out under the same reduced pressure, i.e. protected from oxygen.

The enclosure is maintained at a pressure below atmospheric pressure, preferably below 100 hectopascals and particularly preferably of between 50 and 100 hectopascals.

Thus the above-mentioned preheating makes it possible to establish a pressure and temperature differential in the reduced-pressure enclosure, preferably also forming a refiner, favoring the destruction of the cellular tissues of the pulp, the detachment of the different components of the fruit (skin, pulp and stone) and a fine separation thereof (with the skins and stones remaining whole).

The vacuum is created especially by a vacuum generator set preferably located downstream of the system for recovering and concentrating the aromatic waters originating from the vaporization of part of the vegetation waters coming mainly from the drupe pulp.

The enclosure advantageously also comprises a mechanical device for separating the stones and skins from the pulp, said device comprising for example a rotary filter drum with slots or holes having a width e.g. of between 1 and 2 mm and a diameter e.g. of 2 to 3 mm.

In other words, in the preferred embodiment of the invention, the mechanical separating device is located inside the reduced-pressure enclosure.

In a less advantageous variant, it is possible to insert a reduced-pressure enclosure between the preheating apparatus and the separating device or refiner. In this case, however, the instantaneous and simultaneous effect is lost, the bulk and cost of the equipment are increased and it becomes necessary to remedy the effect of entrainment of pulp particles into the condensation/concentration circuit. Thus, according to the invention, the bursting of the fruits and the physical separation of the stones and skins are preferably carried out in a single reduced-pressure enclosure protected from atmospheric oxidation.

Likewise, the refiner can consist of any other physical means of separation. Here again, however, this would sacrifice an essential effect associated with the rotary drum, whose scrapers and pores make it possible to separate and at the same time refine the pulp to give a "purée" suitable for a direct extraction of the oil contained in the pulp.

In a different mode of carrying out the invention, the scrapers rotate inside a fixed drum. The term "refiner" is used to describe this apparatus according to the invention, but the latter goes well beyond a conventional refiner, being a dual-effect refiner: an effect in two virtually instantaneous steps whereby the pulp is prepared by cell bursting, followed by refining by means of the alveolate drum combined with the scrapers, and by an effect whereby the constituents of the fruit (skin, stone and pulp) are separated.

In this step a number of essential phenomena associated with the invention take place instantaneously and simultaneously.
1) Under the effect of the pressure differential, the water from the mesocarp vaporizes and causes the bursting and destruction of the membranes of the cellular tissues of the drupe pulp.
2) The breaking of the bonds between the skins, pulp and stones of the drupes.
3) The separation of these three components of the drupes, preserving the integrity of the skins and the pulp (pulp on the one hand and skins/stones on the other).
4) The instantaneous cooling of the vegetable matter.
5) The evaporation of the most volatile fractions of the fruit by entrainment associated with the vaporization of the water. It should be noted that the evaporation of the water leads to a loss in weight of the pulp+skins in the order of 8 to 10%. Moreover, this evaporation leads to a virtually instantaneous cooling of the previously preheated pulp and skins.

The process is advantageously carried out continuously until the different products are obtained; it can equally well be carried out batchwise in part, especially as regards the processing of the skins/stones or the pulp (their more or less partial dehydration allowing interim storage without risk of degradation) and less advantageously if all the operations are carried out batchwise.

The skins and stones of the fruit are recovered at the outlet of the refiner and are fed into a receiving trough by any known means, preferably with an eccentric screw, which ensures leaktightness so as not to let down the partial vacuum present in the reduced-pressure enclosure containing the separating device or refiner.

Likewise, the pulp in the form of "purée" is recovered at the bottom of the cone of the refiner and pumped out of the refiner into the downstream equipment, either to separate the oily, aqueous and solid phases or to be used whole. The pump can be of conventional type if the downstream equipment is maintained at the same pressure; otherwise, a pump is used which is capable of preserving the same continuous pressure in the phase separator, in the knowledge that the product in the form of paste creates a "plug" effect between the two media. Between the point where the pulp leaves the refiner and the point where it is taken up by the downstream equipment, an exchanger can preferably be introduced for adjusting the temperature of the mesocarp paste prepared in this way to the temperature desired for all future operations on said paste. Likewise, where the whole pulp leaves the refiner, provision is made for a dryer, especially of the rotary drum type with a scraper, in order to dehydrate the pulp, either for extraction of the oil under pressure (the free aqueous phase has thus been removed by evaporation) or for producing a stabilized whole pulp.

A number of products are obtained after this step:
a) a pulp in the form of purée devoid of skins and stones, said purée being useful as such or dehydrated and being capable of being passed through any known decantation or extraction systems for separating the oily phases from the aqueous phases and solid phases. Said systems are advantageously kept in the same pressure line under a controlled atmosphere in order to avoid any oxidation phenomena. Less advantageously, the system can be outside the controlled atmosphere circuit while at the same time being maintained under an inert atmosphere. Another possibility, as in the present-day industry, is for the systems not to have atmospheric control insofar as rapid separation (of the press or decanter/centrifuge type) does not taint the quality of the products.

In the case of separation, which is the classical method, a pure pulp oil is obtained which is very close to its natural state in the fruit (preservation of the organoleptic characteristics, natural antioxidants and vitamins), together with a partially de-oiled purée containing 3 to 6% of oil and devoid of skins, stones or kernels, which can be utilized in human nutrition and to a lesser extent is of value in animal nutrition.

It should be noted that the novel utilization of this purée makes it possible to control the quantity of oil extracted to optimize its yield in terms of the quality of the oil. In fact, it is known that extraction of the last few percent of oil demands the application of more drastic techniques (pressure, addition of hot water, speed of rotation), the effect of which is to degrade these last few percent of oil, which are in fact mixed with the rest of the extracted oil. Taking into account the value of this partially de-oiled pulp, it is possible to leave a higher proportion of oil (in the order of 10 to 15%) in the pulp in accordance with market demand and the oil will keep all its natural original qualities in this partially de-oiled pulp.

In the case of non-separation, a whole purée is obtained which contains all the components of the pulp and is usable as a human food base. Such is the case of an olive or avocado purée, but at the present time these are obtained by much more drastic technical methods in different industries and always by mechanical processes which induce an oxidation effect detrimental to the quality and preservation of the final product.

b) a mixture of skins and stones extracted from the refiner by any system for maintaining a low pressure in the refiner, advantageously a continuous multiple-chamber system.

After rapid drying on a drum or any other drying means, the whole skins are separated from the whole stones on a cyclone separator-ventilator or any other known system. Depending on the type of drupe, the skins can be utilized in all kinds of ways, either as such or by extraction of a specific component, especially the waxes. The stones are crushed in order to separate the woody shell from the kernel, which must remain whole in order to preserve the integrity assured by its epidermis, it being possible for the woody shells to be utilized in all kinds of ways (power generation, edible bulking agents, industrial applications, etc.). The kernels can advantageously be pressed to extract an oil of high nutritional, cosmetic or pharmaceutical value, such as olive kernel oil or palm kernel oil, often in a substantial proportion in the order of 40%. The press cakes represent a product of high nutritional value and, as in the case of the olive cake, can contain active principles useful in phytotherapy (oleuropein contained in the leaves, which can be concentrated more easily).

c) The most volatile flavors from the drupe, entrained by the vaporization of part of the water from the pulp inside the refiner under partial vacuum, are recovered in a counter-current condenser and concentrated in the "vacuum generator set". These flavors, the finest and most volatile of the fruit, are generally lost in conventional processing operations during the long mixing at a temperature of between 28 and 30°. When recovered and concentrated, they can be used as such or reintroduced into the oil or into the whole or partially de-oiled pulp, according to the consumers' taste or commercial requirements.

According to a second feature, the present invention also provides an apparatus for processing whole oil-producing drupes, particularly olives, oil-palm drupes and avocado drupes, as defined in the independent apparatus claim and, in advantageous embodiments, in the apparatus subclaims.

Furthermore, all the variants of the process which involve equipment characteristics are also covered within the framework of the apparatus according to the invention.

The invention also covers all the products obtained by the process or using the apparatus according to the invention.

The invention also covers an oil-producing drupe pulp oil of improved purity, particularly an olive pulp oil, an oil-palm drupe oil or an avocado drupe oil, which is essentially devoid of kernel oil contained in the stone, and which contains natural antioxidants present in the oil in the native state, especially by being prepared with protection from oxidation, particularly from atmospheric oxygen, this mesocarp or pulp oil being obtainable by the process as defined above or using the apparatus as defined above.

In one advantageous embodiment, the drupe pulp oil also contains at least part of the most volatile compounds of the natural odor of the fruit, especially by having been reintroduced into the final oil, this oil preferably containing the majority of the natural polyphenols and the tocopherol present in the whole fresh fruit, the pure oil advantageously having an acidity, expressed as fatty acid, preferably oleic acid, of less than 1% after storage for two years at ambient temperature, and preferably an acidity, expressed as fatty acid, preferably oleic acid, of less than 0.7 g/100 g of oil after storage for two years at ambient temperature.

The invention also covers, as a product, the kernel oil contained in the drupe stones, and particularly the kernel oil of olives or other drupes such as oil-palm drupes and avocado drupes, said oils being obtainable by carrying out the process described above or using the apparatus described above, as well as the preferred embodiment given by way of example.

The invention also covers a drupe pulp paste obtainable by the process or using the apparatus as described in the present description taken in its entirety, including the example.

The invention also covers the volatile aromatic compounds recovered from drupes, particularly olives, oil-palm drupes or avocado drupes, obtainable by the process or using the apparatus according to the present invention as described in the description taken in its entirety, as well as their use for flavoring the above-mentioned pulp and/or kernel oils and/or the drupe pulp paste.

The invention also covers the use of the drupe pulp oil or drupe kernel oil as described in the present description, i.e. including their recovery by the process or using the apparatus according to the invention, as a foodstuff or a cosmetic or pharmaceutical product.

The present invention also covers the use of the fresh, partially dried or dehydrated drupe pulp paste, essentially de-oiled or containing all its oil, as a foodstuff, especially for human or animal nutrition, after removal of the bitterness.

The invention also covers the use of the woody shells of the stones as a fuel or for the manufacture of an abrasive or a filler, advantageously after mechanical micronization, these woody shells preferably being such as obtained by the process or using the apparatus according to the invention as resulting from the description taken in its entirety.

The invention also covers the use of the kernel press cake as a food source and active principle in the form obtained by the process or using the apparatus according to the invention as resulting from the description taken in its entirety.

It should be noted that FIGS. 1, 2, and 3 form an integral part of the present invention and thus complement the description. Moreover, the invention also comprises any characteristic which appears to be novel relative to any state of the art on the basis of the description taken in its entirety, including FIGS. 1, 2, and 3; these novel characteristics are claimed in their function and their generality.

The invention will be understood more clearly in its advantages and its characteristics from the following description referring to a currently preferred embodiment of the invention, which forms an integral part of the invention in its generality, with reference to FIGS. 1, 2 and 3 attached.

Figure 2:
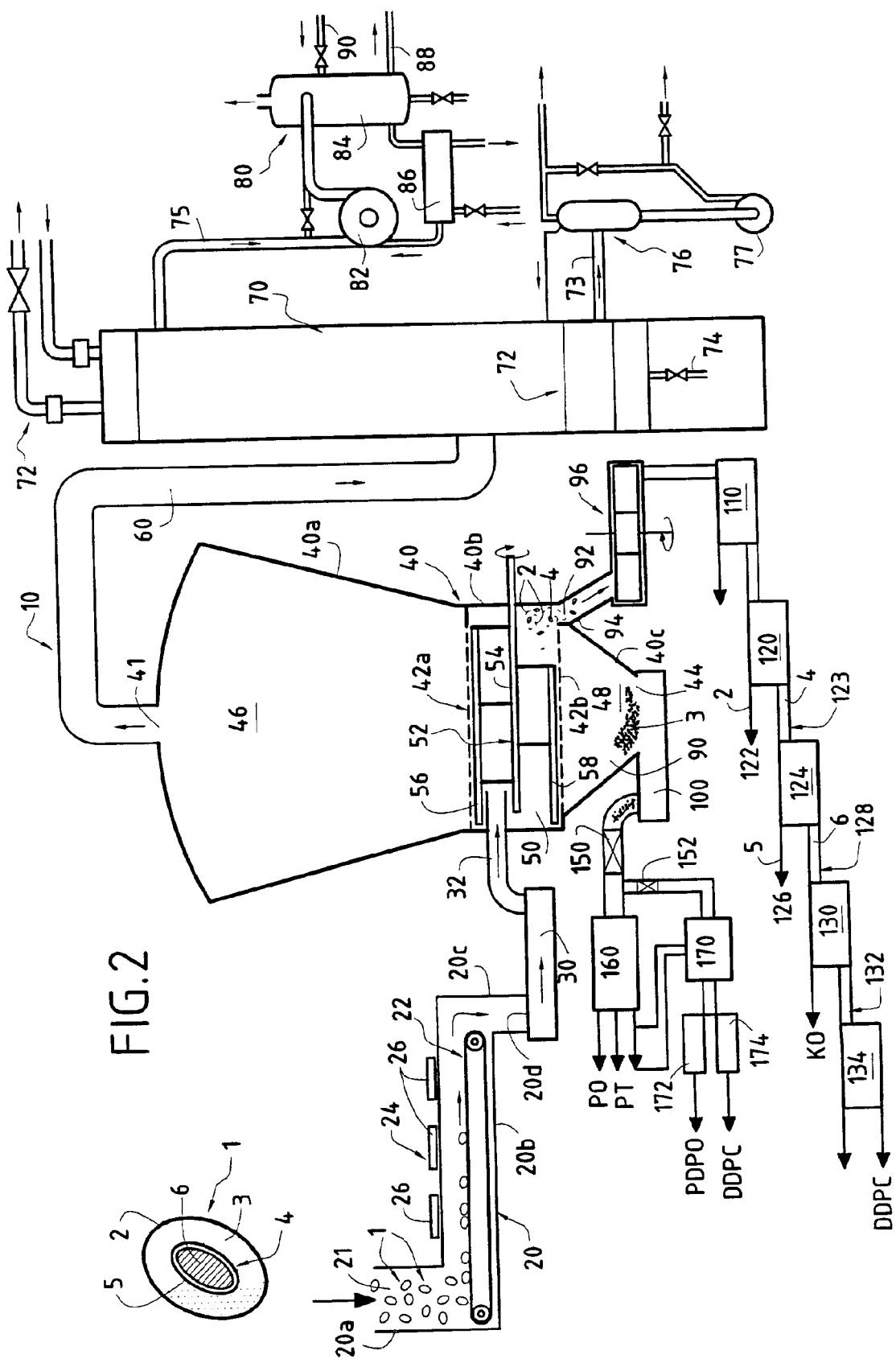
FIG. 2 is a diagrammatic representation of the essential parts of a first embodiment of an apparatus for the processing of whole drupes according to the present invention, general reference number 10, in vertical axial cross-section, including a separation apparatus mounted according to a substantially horizontal axis.
Figure 3:
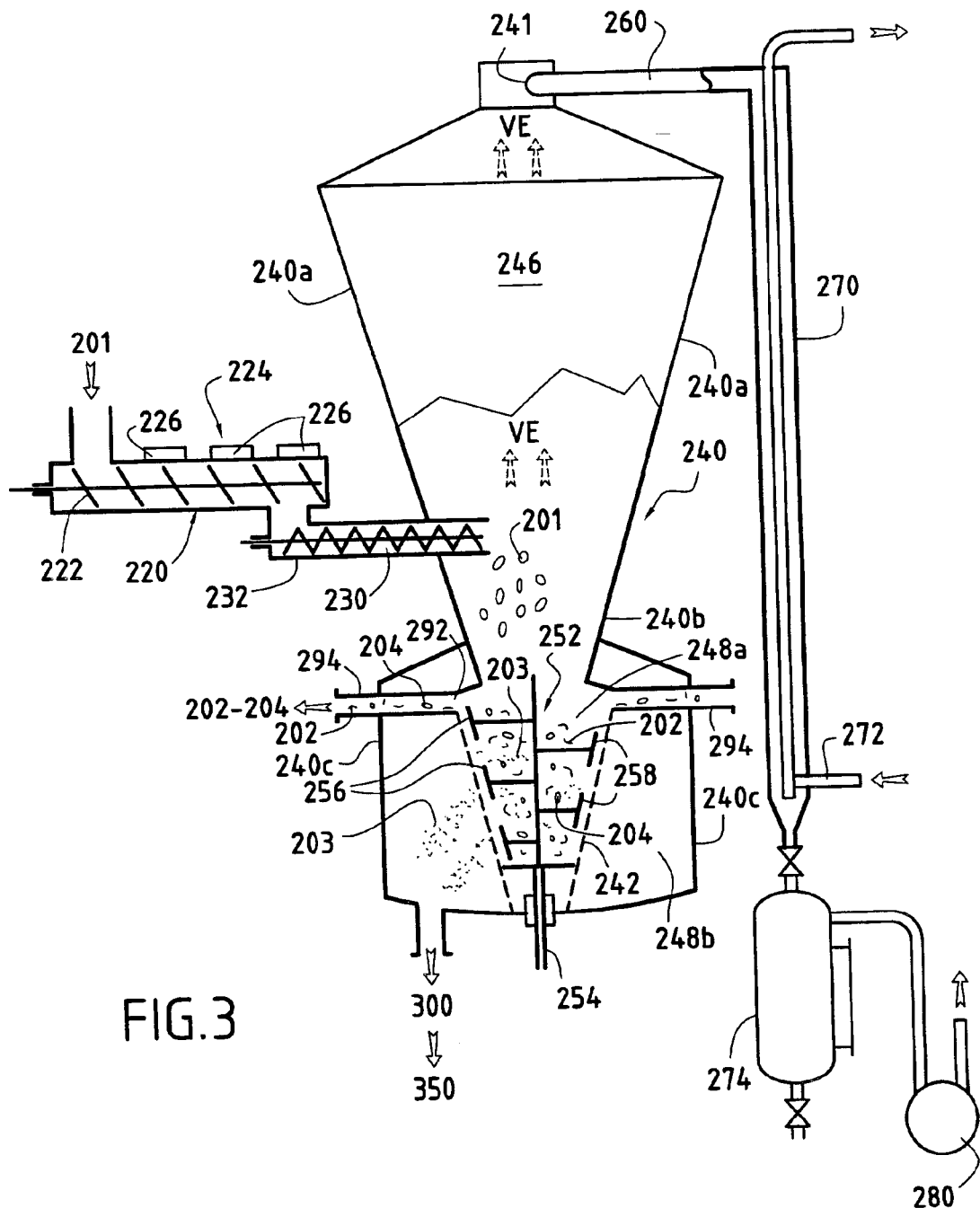

FIG. 3 is a diagrammatic representation similar to the FIG. 2 of the essential parts of an apparatus for the processing of whole drupes according to a second variant embodiment of the present invention, in vertical axial cross-section, wherein the rotation axis of the separation apparatus is substantially vertical. The apparatus parts located downward of the separation apparatus are identical to the parts of the FIG. 2 and are not shown.

Figure 1:
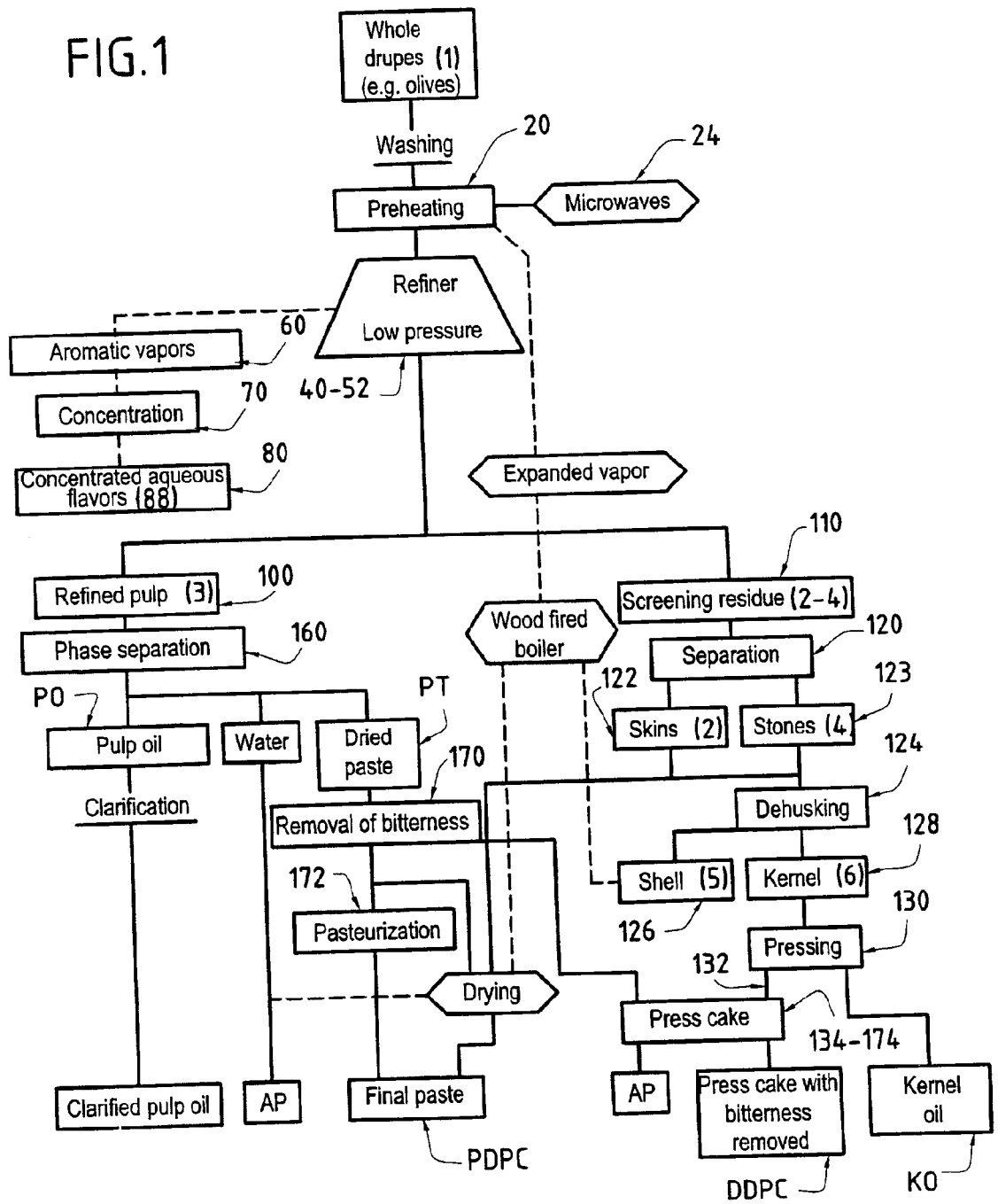
FIG. 1 is a basic diagram of the steps involved in the processing of whole drupes according to the present invention, which can be carried out with the apparatus forming the subject of FIG. 2 or 3.

With reference to FIGS. 1 and 2, the apparatus for the processing of whole drupes according to the present invention has the following characteristics:

The whole drupes 1 are composed of the epicarp or skin 2, the mesocarp or pulp 3 and the endocarp or stone 4, which in turn is composed of an envelope 5, commonly called a shell, composed of wood fibers and containing a kernel 6 inside. For a clearer understanding of its structure, this whole drupe is shown enlarged in FIG. 2.

These whole drupes are generally and preferably fresh since they then contain a greater proportion of water, which is also exploited within the framework of the present invention, as is apparent from the definition of the process and apparatus in the foregoing and following descriptions, with reference to the apparatus of FIG. 2.

Thus the whole drupes 1 are introduced, preferably after washing, into a heating or preheating enclosure 20, which can comprise a vertical part 20a, constituting a kind of hopper for receiving and storing the whole drupes 1, and a part 20b which can be essentially horizontal, as shown, and which houses a device for advancing the whole drupes, such as a conveyor belt 22, transferring the whole drupes from the upstream part 20a into a downstream part 20c, in this case vertical, which can be open at the bottom and have a discharge orifice 20d for transferring the whole drupes leaving the preheating enclosure 20 into an intermediate buffer enclosure 30, which will be described below.

According to the present invention, the preheating enclosure 20 is provided with preheating means 24 which, in the preferred embodiment shown in FIG. 2, comprise several microwave emitting devices 26, the purpose of which is to heat the water molecules contained in the mesocarp of the whole drupes to a predetermined temperature advantageously of between 80 and 90° C. It is possible, for example, to use a customary microwave frequency of about 2450 MHz or, in some cases, of about 915 MHz, on condition that this frequency is authorized.

In fact, as will become apparent from the description below, this temperature is preferred because it subsequently allows the rapid or virtually instantaneous vaporization of a fraction of the vegetation water.

The whole drupes, whose pulp has been preheated in the preheating enclosure 20, are collected in the intermediate enclosure 30, which is provided as a buffer enclosure creating a seal relative to the preheating enclosure 20, the leaktightness normally being assured by the presence of a continuous transfer device, preferably with an eccentric screw, forming a plug of material in order to isolate it from the atmospheric pressure prevailing in the preheating enclosure 20 by virtue of the inlet orifice 21 for the whole drupes.

The whole drupes, with their pulp preheated, are then transferred from the intermediate enclosure 30 into a sealed reduced-pressure enclosure 40 by any transfer means well known to those skilled in the art, for example by means of a screw system present in the transfer duct 32, which in this case comes out into a part 40b of the reduced-pressure enclosure 40. The enclosure 40 is subdivided into the following three parts:

a) The top part 40a of the reduced-pressure enclosure 40, preferably in the shape of an inverted truncated cone, defines a chamber 46 serving as an expansion chamber for the vapors emitted under reduced pressure and entraining the vaporized volatile flavors, which are transferred, via an upper orifice 41 communicating with a transfer duct 60, into a condenser 70, also under reduced pressure, in which the partial vacuum is created by a vacuum generator set 80 well known to those skilled in the art. The purpose of the preferably inverted conical shape of the top part 40a of the enclosure is to slow down the emitted vapors and hence to prevent the entrainment of solid particles.

In the condenser 70, the cooling is effected with the aid of a conventional countercurrent indirect cooling circuit 72, a discharge valve 74 being provided at the bottom of the condenser. The substantially non-flavored, condensed water collected at the bottom of the condenser 70 is drawn off by a withdrawal and recovery device 76, which also has a duct for recycling into the condenser 70 to ensure stabilization of the hydraulic level. This device 76 comprises a circulating pump 77.

Furthermore, at the top of the condenser 70, the water vapors containing the concentrated flavors are drawn off via the duct 75, being sucked by the device 82, such as a liquid ring vacuum pump, and introduced into a concentrating device 80, for example a cyclone separator 84, to give concentrated aqueous flavors at the bottom of the separator 84; these are drawn off via the duct 88 and can be used as such or for flavoring the oils obtained, for example the pulp oils or kernel oils, or the pulp paste obtained elsewhere. A duct 90 for supplying water at the start of the operating cycle can be provided at an intermediate level. In addition, the top of the cyclone separator 84 can be in communication with the atmosphere. A device 86 is also advantageously provided for circulating water in a cooled closed circuit feeding the liquid ring pump 82.

b) The intermediate part 40b is delimited by the presence of upper and lower separating means, 42a and 42b respectively, which preferably consist of filter meshes forming screens, for example of a perforated cylinder, in this case fixed or capable of rotating, having orifices which comprise slots or openings of appropriate size for allowing the drupe endocarp or pulp to pass through and stopping the drupe skins and stones in order to carry out their physical separation.

In this example, the intermediate part 40b of the enclosure 40 also houses an agitating device, such as 52, for favoring a physical separation of the different constituents of the whole drupes, said device in this case comprising e.g. a rotating horizontal shaft fitted with scraper blades 56, 58, cooperating with the cylinder 42 which is here of stationary, fixed position. The blades 56, 58 are advantageously of offset length to favor shear effects and hence the physical separation of the pulp from the stones. According to a variant, the agitating device can also comprise a rotatingly mounted, perforated cylinder 42 integral with the shaft 54, the scraper blades 56, 58 being of fixed, stationary position to obtain the same scraping and shear effects.

c) The bottom part 40c of the enclosure 40 defines a chamber 48 for collecting the pulp passing through the cylinder 42, which turns into a purée under the effect of the virtually instantaneous evaporation of the water contained in the pulp, culminating in a destructuring of the whole drupes with bursting of the pulp. The purée formed in this way comprises a mixture of oil, pulp cell debris, water, skins and whole stones.

The pulp purée 3 recovered in the chamber 90, which is filtered by the cylinder 42, is collected at the bottom of the bottom part 40c of the enclosure 40 and accumulated in a specific transfer enclosure 100, this purée being substantially or essentially devoid of whole stones and waxy skins.

The mixture of skins 2 and stones 4 is separated off and ends up at a lateral discharge orifice 92 communicating via a duct 94 with a transfer device 96, for example with a rotary pitch.

The transfer device 96 constitutes a rotary pitch system which also ensures a seal similar to that of the intermediate enclosure 30, so as to preserve the partial vacuum present in the enclosure 40.

Within the framework of the invention, the top part 40a of the partially evacuated enclosure 40 advantageously has the shape of an inverted truncated cone so as to restrict the speed of entrainment of the vapors. The partial vacuum prevailing in the enclosure 40 is advantageously below 100 hectopascals and preferably between 50 and 100 hectopascals.

The mixture of skins 2 and stones 4 is then sent to an intermediate storage enclosure 110, where they can optionally be dried and stored for subsequent processing in order to separate them, which can be effected by any known means such as a cyclone ventilator 120. On the one hand this gives the skins 2 at the outlet 122, which can themselves be ground for use as cattle feed or can be processed specifically for the extraction of particular products such as the waxes.

As far as the stones 4 are concerned, these are sent via the duct 123 to a device 124 for crushing or grinding with devices well known to those skilled in the art, which make it possible to separate off on the one hand the woody shells 5, recovered at 126, and on the other hand the kernels 6 at the outlet 128, which in this case remain whole with their protective film.

The woody shells 5 are recovered at 126 and constitute an energy source for the enterprise, making it possible to favor a calorific balance which ensures that the process and apparatus are self-sufficient in energy terms.

The kernels 6 recovered via the outlet 128 can advantageously be sent to a pressing device 130, affording on the one hand a kernel oil KO, which can be used as such in nutrition, cosmetics and pharmacy, kernel oil being well accepted and, in the case of olive kernel oil for example, being closely related to codex sweet-almond oil with its inherent presence of squalene.

After pressing in the pressing device 130, the remaining tissues are called press cakes and are discharged at 132 for storage at 134. These cakes 134 represent about 60% of the total initial matter and the richness in protein (30% of mad) and its amino acid composition make them comparable to groundnut cakes and another source usable for human and animal nutrition.

It is also recommended to extract, in the device 134, a concentrated bitter active principle which, in the case of olive drupe processing, comprises mainly oleuropoeoside; this is also present in the leaves of the olive tree and is well known in phytotherapy for its vasodilating and hypotensive effects.

Furthermore, the pulp 3 stored in the transfer enclosure 100, which is essentially devoid of skins and stones, is transferred by means of any transfer device, for example a simple pump (not shown), into an exchange device of the tubular type, such as 150, especially for the purpose of bringing it to the appropriate temperature for extraction operations.

The pulp 3 coming from the enclosure 100 can thus be subjected to separation of the aqueous, oily and solid phases by any pressing, centrifugation or natural or forced decantation method in the separating device 160.

It should be noted that the pulp purée 3 is obtained within the framework of the invention without an emulsion, making its processing more efficient.

A pure pulp oil PO is obtained at the outlet of the separating device 160. Partially de-oiled pulp tissues PT are also obtained and these can optionally be pasteurized and/or dehydrated to a greater or lesser extent.

In one variant, after passing through the device 150, the pulp purée 3 can be transferred via the valve 152 into a device 170 in which more or less of the bitterness is removed, depending on the maturity of the fruit, and then pasteurized in a pasteurizing device 172 to form a pasteurized pulp oil from which the bitterness has been removed, PDPO, while the tissues can be treated in a drying device 174 to give a dehydrated pulp cake from which the bitterness has been removed, DDPC.

With reference to FIG. 3, the apparatus for the processing of the whole drupes according to a second embodiment of the present invention, has been modified in comparison to the apparatus shown in FIG. 2 in order to present a separation mean of stone and skin from the pulp, including a substantially vertical rotation axis in opposition to FIG. 2 which rotation axis is substantially horizontal. Otherwise, the downward parts of the separation apparatus are not drawn in FIG. 3 and are identical to the parts of FIG. 2, in order to simplify the drawing. Therefore, the same reference numbers, as those used in FIG. 2, are used for the embodiment of FIG. 3 for the same parts identical or similar, but increased of 200 in order to avoid mistake between the two embodiments.

Therefore:

The whole drupes 201 are introduced, preferably after washing, into a heating or preheating enclosure 220, which is provided with preheating means 224, which can comprise several microwave emitting devices 226 like the first embodiment of the FIG. 2. Inside the preheating enclosure 20, a device for advancing the whole drupes 222 is housed for example here a endless screw, for transferring the whole drupes into an intermediate buffer enclosure 230, similar to the intermediate buffer enclosure 30 of FIG. 2, but here constituting at the same time an introduction pipe for transferring the whole drupes into the sealed reduced-pressure enclosure 240, like reduced-pressure enclosure 40, comprising a pipe 232 similar to pipe 32.

In this second embodiment, the sealed reduced-pressure enclosure 240 comprises a top part 240*a* similar to part 40*a* of the sealed reduced-pressure enclosure 40, an intermediate part 240*b* localised around the introduction level of whole drupes through the pipe 232, and a bottom part 240*c* similar to part 40*c* of FIG. 2.

In this embodiment, the whole drupes are introduced at an intermediary level of sealed reduced-pressure enclosure 240, which allows to make the whole drupes falling under the gravity effect by being furthermore physically fluidized, helping the evaporation of enclosed water present in the pulp tissues for producing an evaporation under a stream form of water vapor shown by arrows VE ascending inside the sealed reduced-pressure enclosure and in particular up through the top part 240*a* for going outside in direction to the pipe 260 similar to pipe 60 of FIG. 2.

It is emphasized therefore that this embodiment of FIG. 3, in comparison to FIG. 2, is different through the falling during a few second fractions of whole drupes inside the enclosure around its intermediate level 240*b* by facilitating the water evaporation contained in the pulp which has been preheated through the preheating mean 220 and precisely in a preferred embodiment by microwave means 224–226. As it was described in the first embodiment, the evaporation quasi instantaneous of the water contained in the pulp gives a cellular destructuration of the pulp.

The whole drupes having their water quasi instantaneously evaporated falls into the bottom part 240*c* of enclosure 240, defining a separation chamber 248*a*, 248*b*, which comprises a stirring means 252 similar in its function to the stirring mean 52 of FIG. 2, but which comprises here a substantially vertical rotation axis instead of an horizontal axis like in FIG. 2. The rotation axis presents a reference number 254 and corresponds to the rotation axis 54 of FIG. 2 and can be linked to scraper blades 256 and 258 similar to scraper blades 56 and 58 of FIG. 2, cooperating here with a stationary cylinder filtration device 242, linked to enclosure 240*c*, similar to cylinder filter device 42 of FIG. 2, and which is in preference with an inverted truncated cone form in order to obtain a narrower bottom part and a larger top part. The scraper blades 256 and 258, which are advantageously of offset length, like the other embodiment, to favor shear effects and hence the physical separation of the pulp from the stones. Like the embodiment of FIG. 2, in a variant, the stationary part and the rotative part can be exchanged each other, the filtration cylinder 242 can be rotative and the scraper blades can be stationary. It should be noted that the filtration cylinder 242, which has the same function as the cylinder 42 of FIG. 2 allows to filter on one hand the pulp purée 203, which comprises a mixture of oil, pulp cell debris, and water; and, on the other hand, to retain because there are not filtered, the skins 202 and the stones 204, which latter are, under stirring effect of scraper blades 256 and 258 or of variant rotating filter, progressively been removed to the top for being evacuated through the orifice 292 and the pipe 294, similarly to orifice 92 and pipe 94 of FIG. 2 for being then treated like in the embodiment of FIG. 2. This evacuation is eased by an unshown withdrawal pump or similar. This pulp 203 purée, now stored in chamber 248*b* defined between the filter device 242 and the enclosure wall 240*c*, which comprises the mixture of oil, pulp cell debris, and water, is extracted through the bottom part 240*c* of enclosure 240 through a pipe for eventually feeding an intermediate storage enclosure symbolically referenced 300 similar to storage enclosure 100 of FIG. 2 then a heat transfer device 350 similar to device 150 of FIG. 2, the rest of the separation treatment, which comprises on one hand separation of pulp oil, pulp water and pulp cell debris, and on the other hand skins and stones, is the same or similar as with the other embodiment of FIG. 2.

Within the framework of the invention, it can be observed that, if the equipment downstream of the reduced-pressure enclosure 40 is not capable of processing the quantities of whole drupes harvested, it is possible to remove an aliquot of the whole prepared purée 100 from the remainder of the processing operation and keep it in troughs in the cold, at a temperature of between 2 and 4° C., and under a controlled atmosphere for processing at a later stage, thereby giving the industry a greater independence from its seasonal nature and making it possible to work over a larger part of the year.

This purée is easier to store than the whole drupes by virtue of its reduced bulk and, at the same time, it is infinitely easier to control good keeping conditions.

Thus it is seen that the invention makes it possible to recover all the constituents of oil-producing drupes. The apparatus which has now been described, and the process for operating it in the essential steps shown in FIG. 1, are applicable to all oil-producing drupes.

Within the framework of the invention, the preferred oil-producing drupes are olives, oil-palm drupes or fruits and avocado fruits or drupes.

With palm drupes or fruits, the products are primarily an extremely pure oil derived from the pulp, called "palm oil", and an oil derived from the kernel of the stone, called "palm kernel oil", whereas with avocado drupes, the products are two avocado oils derived respectively from the pulp and from the kernel of the stone.

It should be pointed out that, for avocados, the process and apparatus according to the invention make it possible to obtain a whole pulp purée under continuous rapid conditions which avoid oxidation, said purée serving as a food base for a number of specific human foodstuffs.

Finally, the prior separation of the skins and stones from the pulp makes it possible to utilize all the co-products while at the same time restricting the constitution of liquid or solid polluting effluents, which ultimately become a financial burden on the enterprise and/or the environment.

Thus the invention makes it possible to solve the above-mentioned technical problems and to arrive at a solution which constitutes a decisive technical advance that is particularly unexpected for those skilled in the art.

In the currently preferred embodiment of the processing of olives as oil-producing drupes, Tables no. 1 to 5 below show the weights of the various constituents, their proportions by weight and the calorific balance per 100 kg of fresh whole olives processed.

TABLE NO 1

Average composition of OLIVES (per 100 kg)

|  |  | Pulp |  | Skins |  | Kernels |  | Shells |  | Total |
|---|---|---|---|---|---|---|---|---|---|---|
| Water | kg | 41 |  | 1.6 |  | 0.3 |  | 1.5 |  | 40 to 50 |
|  | % |  | 55 |  | 20 |  | 15 |  | 10 |  |
| Oil | kg | 18 |  | 0.7 |  | 0.7 |  | 0.3 |  | 18 to 25 |
|  | % |  | 24 |  | 10 |  | 35 |  | 2 |  |
| Solids | kg | 16 |  | 5.6 |  | 1 |  | 13.2 |  | 30 to 40 |
|  | % |  | 21 |  | 70 |  | 50 |  | 88 |  |
| Total | kg | 75 | — | 8 | — | 2 | — | 15 | — |  |
|  | % | — | 100 | — | 100 | — | 100 | — | 100 | 100 |

TABLE NO 2

Pulp after integral processing (of 100 kg of olives)

|  |  | Pulp |  | Skins |  | Kernels |  | Shells |  | Total |  |
|---|---|---|---|---|---|---|---|---|---|---|---|
| Water | kg | 36 |  | 1.5 |  | 0.3 |  | 1.5 |  | 39 |  |
|  | % |  | 51 |  | 19 |  | 15 |  | 10 |  | 41 |
| Oil | kg | 18 |  | 0.8 |  | 0.7 |  | 0.3 |  | 20 |  |
|  | % |  | 26 |  | 10 |  | 35 |  | 2 |  | 21 |
| Solids | kg | 16 |  | 5.6 |  | 1 |  | 13.2 |  | 36 |  |
|  | % |  | 23 |  | 70 |  | 50 |  | 88 |  | 38 |
| Total | kg | 70 | — | 8 | — | 2 | — | 15 | — | 95 | — |
|  | % | — | 100 | — | 100 | — | 100 | — | 100 | — | 100 |

TABLE NO 3

Comparison of whole pulp and pulp after extraction

| Per 100 kg of olives |  | Whole pulp | De-oiled pulp |
|---|---|---|---|
| Water | kg | 32 | 13 |
|  | % | 49 | 43 |
| Oil | kg | 18 to 20 | 2 to 5 |
|  | % | 28 | 7 |
| Solids | kg | 15 | 15 |
|  | % | 23 | 50 |
| Total | kg | 68 | 30 |
|  | % | 100 | 100 |

TABLE NO 4

Products derived from integral processing of olives

| Product | Weight | % water |
|---|---|---|
| Pulp oil | 18 to 20 kg | 0% |
| Kernel oil | 0.8 to 2 kg | 0% |
| De-oiled pulp | 30 to 35 kg | 30% |
| Kernel press cake | 1.2 to 3 kg | 30% |
| Woody shells of stones | 17 to 23 kg | 20% |
| Aqueous flavors | 8 to 10 kg | 99% |
| Skins | 1.5 to 2 kg | 30% |
| Vegetation waters | 20 to 25 kg | 100% |

TABLE NO 5

Processing of 100 kg of olives
CALORIFIC BALANCE
(Mean Values)

|  |  |  |  | KW-H |
|---|---|---|---|---|
| Woody shells of stones |  |  | 18 kg |  |
| Calorific power |  |  | 4000 Kcal/kg |  |
| Calories theoretically available |  |  | 72,000 Kcal | 83.7 |
| If thermal efficiency is |  | 70% | 50,400 Kcal | 58.6 |
| Calories for preheating olives (skins + pulp) | 80 k × 0.75 × (90° − 10°) = |  | 4800 Kcal | 5.6 |
| Calories for evaporating water of constitution (skins + pulp) | 34 k × 600 = |  | 20,400 Kcal | 23.7 |
|  |  | TOTAL | 25,200 Kcal | 29.3 |
| Remainder available = |  |  | 25,200 Kcal | 29.3 |
| Corresponding theoretical evaporating capacity = |  |  | 42 kg of water |  |

It is therefore possible to use up to 40 liters of water to wash or remove the bitterness from the marc originating from 100 kg of olives, without having to discard the effluent, if the mill is equipped with a dryer or an evaporator. Conversely, half of the woody shells of the stones would remain available for conversion to fillers and abrasives.

What is claimed is:

1. A process for the processing of fruits of the type comprising whole oil-producing drupes with skins, pulp and stones containing kernels, said process comprising the steps of:
   a) preheating the whole drupes under controlled conditions for carrying out a controlled preheating limited to the water contained in the pulp, and under conditions which substantially avoid the oxidation of the pulp's natural antioxidants;
   b) effecting a rapid or virtually instantaneous evaporation of a fraction of the preheated water contained in the pulp, favoring cellular destructuring limited to the pulp with incipient detachment of the pulp from the skins and stones, under conditions which substantially avoid the oxidation of the pulp's natural antioxidants;
   c) separating and recovering the pulp resulting from the cellular destructuring due to the partial evaporation of the water, essentially devoid of stones and skins, and of the stones with skins, essentially devoid of pulp, respectively;
   d) separating pulp oil and the destructured pulp in the form of partially de-oiled purée, respectively; and
   e) recovering the pulp oil essentially devoid of oil derived from the stones and skins and containing the pulp's natuaral antioxidants, thereby improving the oxidation resistance of said oil.

2. The process according to claim 1 wherein the preheating is carried out in a heating enclosure protected from oxidation, in a predetermined temperature range and for a predetermined period of time which entail substantially no risk of degradation of the pulp, this preheating step effected by means of any direct or indirect heating system.

3. The process according to claim 1 wherein the preheating is effected by microwave emission so that the temperature reached by the water contained in the pulp is sufficient to favor the rapid or virtually instantaneous evaporation of the fraction of said water in the evaporation step b), the preheating being effected in a heating enclosure so that the temperature reached by the water contained in the pulp is in the order of 80° C. to 90° C.

4. The process according to claim 1 wherein the preheated whole drupes are transferred into an evaporation enclosure maintained at a pressure below atmospheric pressure, in which the evaportation of the fraction of the water contained in the pulp produces the cellular destructuring with incipient formation of a purée containing the oil, with cooling, and the remaining water and cellular tissues resulting from the burst or disaggregated pulp, together with the whole stones and the skins.

5. The process according to claim 1 wherein the destructured pulp and the whole stones and the skins are separated in a separator or refiner, said separator or refiner completing by means of agitation or mechanical friction, the physical refining of the cellular tissues of the pulp and the release and coalescence of the oily formations contained in the destructured pulp, and promoting completing the physical separation of the destructured tissues of the pulp remaining on the stones.

6. The process according to claim 5 wherein, the separator or refiner comprises a rotary screen protected from the air.

7. The process according to claim 5, wherein the separator or refiner comprises a rotary screen working under a partial vacuum or an inert atmosphere.

8. The process according of claim 1, wherein the pulp in the form of purée resulting from its cellular destructuring, separated from the stones and skins, is subjected to a phase separation of a solid phase, an aqueous phase, if still present, and an oily phase to give the pulp oil which is essentially pure and essentially devoid of stone oil, kernel oil and skin oil, and which is also substantially devoid of the flavors and tastes peculiar to them.

9. The process according of claim 8, wherein this phase separation is carried out after the purée has passed through a heat exchanger, which controls the temperature of the purée and/or effects a controlled dehydration to substantially completely remove the remaining aqueous phase by evaporation.

10. The process according of claim 1, wherein the stones are separated from the skins by a physical process of separation.

11. The process according of claim 10, wherein said physical process of separation is selected from the group consisting of a process involving meshes of appropriate size, a process involving vibration and a process involving ventilation.

12. The process according of claim 11, wherein said physical process of separation is taking place after the stones and skins have been dried.

13. The process according to claim 10, wherein the stones separated from the skins are then mechanically ground so as to separate a woody shells of the stones from the kernels contained in the stones, which remain whole with their protective epidermis, the kernels being processed by means of an extraction system used to extract oils from the kernels under pressure, to give a kernel oil of high cosmetic and pharmaceutical value, and a press cake of high nutritional value formed by the at least partially de-oiled tissues of the kernel, which are recovered.

14. The process according to claim 13, wherein the cake is processed further to give an extract and a bitter active principle for medicinal use.

15. The process according to claim 13, wherein olives are processed and the olive cake is processed further to give an extract and a bitter active principle comprising oleuropein.

16. The process of claim 4, wherein the most volatile compounds of the natural odor of the oil-producing drupes, which volatilize in the evaporation enclosure maintained under low pressure, are recovered, by being condensed and concentrated continuously at an outlet of the evaporation enclosure.

17. The process of claim 16, wherein at least a part of the most volatile compounds, recovered, condensed and concentrated, are introduced into the finished oil product, according to different consumers' tastes.

18. The process according to claim 4, wherein the sub-atmospheric pressure ranges between 50 and 100 hectopascals.

19. The process according to claim 1, wherein the oil-producing drupes processed are selected from the group consisting of olives, oil-palm drupes and avocados.

20. An apparatus for the processing of whole oil-producing drupes with skins, pulp and stones containing kernels, said apparatus comprising:
 a) at least one device for preheating the whole drupes which effects a preheating limited to the water contained in the pulp under conditions which substantially avoid the oxidation mainly of the pulp's natural antioxidant;
 b) at least one sealed enclosure for rapid or virtually instantaneous evaporation of at least part of the water contained in the whole drupe pulp, under conditions which substantially avoid the oxidation mainly of the pulp's natural antioxidants, said rapid or virtually instantaneous evaporation effecting a physical destructuring of the cellular tissues of the pulp with incipient detachment of these destructured cellular tissues from the skins and stones;
 c) at least one first separation device for the physical separation and recovery of the pulp essentially devoid of stones and skins, and of the stones and skins essentially devoid of pulp, under conditions which substantially avoid oxidaiton,
 d) at least one second separation device for the separation and recovery of pulp oil essentially devoid of stone oil and containing the drupe pulp's natural antioxidants, and of a substantially de-oiled pulp.

21. The apparatus according to claim 20, further comprising at least one third separating device for separating the skins from the stones.

22. The apparatus according to claim 21, further comprising at least one grinding or crushing device for mechanically grinding or crushing the stones to produce woody shells of the stones under conditions which preserve the integrity of the kernels contained in the stones, these kernels remaining whole in their epidermis, and at least one device for mechanically separating the woody shells of the stones from the kernels.

23. The apparatus according to claim 22, further comprising at least one extracting device for extracting oil contained in said separated kernels.

24. The apparatus according to claim 23, wherein said at least one extracting device comprises a pressing device, with recovery of the oil from the kernels and of a press cake.

25. The apparatus according to claim 24, wherein said press cake is subjected to a further extraction device for extraction of a bitter active principle.

26. The apparatus according to claim 25, wherein olives are processed and the bitter active ingredient comprises oleuropein.

27. The apparatus according to claim 20, wherein the device for preheating the whole drupes comprises means of heating with the aid of microwave emitters, which are intended to heat the water contained at least in the pulp to a temperature of between 80 and 90° C.

28. The apparatus according to claim 20, wherein the first separation device for physical separation is located in said sealed enclosure.

29. The apparatus according to claim 20, wherein the sealed evaporation enclosure is maintained at a pressure below atmospheric pressure, in which the evaporation of the fraction of the water contained in the pulp produces the cellular destructuring with incipient formation of a purée containing the oil, with cooling, and the remaining water and cellular tissues resulting from the burst or disaggregated pulp, together with the whole stones and the skins.

30. The apparatus according to claim 20, wherein at least one of the first separation device comprises a screening device provided with a screen located in said sealed evaporation enclosure working under a partial vacuum or an inert atmosphere, said screening device being physically located in said sealed enclosure to provide a bottom enclosure part defining a chamber for collecting the pulp passing through the screen turning in the form of a puree, whereas the skins and stones are separated off by the screen and exit the sealed enclosure at a discharge office for further separation.

31. The apparatus according to claim 20, wherein the at least one second separation device is subjecting the pulp in the form of a purée resulting from its cellular destructuring, separated from the stones and skins, to a phase separation of a solid phase, an aqueous phase, if still present, and an oily phase to give the pulp oil which is essentially pure and essentially devoid of stone oil, kernel oil and skin oil, and which is also substantially devoid of the flavors and tastes peculiar to them.

\* \* \* \* \*